US00PP24033P3

(12) United States Plant Patent

Klemm et al.

(10) Patent No.: US PP24,033 P3

(45) Date of Patent: Nov. 19, 2013

(54) *OSTEOSPERMUM* PLANT NAMED 'KLEOE11189'

(50) Latin Name: ***Osteospermum ecklonis* Norl.**
Varietal Denomination: KLEOE11189

(75) Inventors: Nils Klemm, Stuttgart (DE); Sankalp Bhosale, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 89 days.

(21) Appl. No.: 13/506,066

(22) Filed: Mar. 23, 2012

(65) Prior Publication Data

US 2013/0254955 P1 Sep. 26, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Annette Para

(74) *Attorney, Agent, or Firm* — Jondle Plant Sciences Division of Swanson & Bratschun, L.L.C.

(57) ABSTRACT

An *osteospermum* variety named 'KLEOE11189' particularly distinguished by a spreading growth habit and good branching, is disclosed.

1 Drawing Sheet

Genus and species: *Osteospermum ecklonis* Norl.
Variety denomination: 'KLEOE11189'.

BACKGROUND OF THE NEW PLANT

The present invention comprises a new and distinct variety of *osteospermum*, botanically known as *Osteospermum ecklonis* Norl., and hereinafter referred to by the variety name 'KLEOE11189'. The new variety originated from a controlled cross conducted in May 2008 in Nairobi, Kenya. The female parent was *osteospermum* plant named 'KLEOE09175' (U.S. Plant Pat. No. 22,054), and the male parent was *osteospermum* plant named 'OE 06 0119' (unpatented). A single plant selection was subsequently chosen for further evaluation and asexual propagation.

The new variety was first propagated via vegetative cuttings in May 2009 in Stuttgart, Germany and has been asexually reproduced repeatedly by vegetative cuttings over three to four generations. The present invention has been found to retain its distinctive characteristics through successive asexual propagations via vegetative cuttings.

'KLEOE11189' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Spreading growth habit; and
2. Good branching.

DESCRIPTION OF THE PHOTOGRAPH

This new *osteospermum* plant is illustrated by the accompanying photograph; the colors shown are as true as can be reasonably obtained by conventional photographic procedures.

The photograph was taken in spring 2011 on a 3-month old plant grown in a heated glass greenhouse in Stuttgart, Germany, under conditions which approximate those generally used in normal horticultural practice.

DESCRIPTION OF THE NEW VARIETY

The following detailed descriptions set forth the distinctive characteristics of 'KLEOE11189'. The data which define these characteristics were collected from asexual reproductions carried out in Stuttgart, Germany. The plant history was taken in the spring of 2011 on three-month old plants grown in 12 centimeter pots. The plants were grown in a glass greenhouse and pinched once. Color readings were taken under natural and artificial light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Asteraceae.
- *Botanical name.*—*Osteospermum ecklonis* Norl.
- *Common name.*—African daisy.
- *Denomination.*—'KLEOE11189'.

Parentage:
- *Female parent.*—*Osteospermum* plant named 'KLEOE09175' (U.S. Plant Pat. No. 22,054).
- *Male parent.*—*Osteospermum* plant named 'OE 06 0119' (unpatented).

Plant:
- *Form and habit.*—Herbaceous perennial, usually cultivated as an annual.
- *Growth habit.*—Medium vigor.
- *Branching habit.*—Freely branching.
- *Height (from top of soil).*—24.0 cm.
- *Width (including inflorescence).*—22.0 cm.
- *Propagation.*—Vegetative cuttings from tips.

*Time to produce a finished flowering plant.*—14 to 16 weeks.
*Time to initiate and develop roots.*—3 to 4 weeks.
*Root description.*—Freely rooting.

Leaves:
*Arrangement.*—Arranged in a whorl.
*Shape.*—Dentiform.
*Apex.*—Acute.
*Base.*—Acute.
*Margin.*—Serrate.
*Color.*—Immature leaf: Upper surface: RHS 137B. Lower surface: RHS 137A. Mature leaf: Upper surface: RHS 137A. Lower surface: RHS 137B.
*Length.*—2.4 cm.
*Width.*—2.2 cm.
*Texture.*—Leathery.
*Petiole.*—Absent.

Stems:
*Total number of branches.*—4 to 6.
*Length.*—18.0 cm to 19.0 cm.
*Diameter.*—0.4 cm.
*Internode length.*—1.1 cm to 1.8 cm.
*Color.*—RHS 137B.
*Texture.*—Smooth.

Inflorescence buds:
*Shape.*—Obovate.
*Length.*—1.3 cm.
*Diameter.*—1.1 cm.
*Color* (*at tight bud just before the ray florets unfold*).—RHS 137B.

Inflorescence:
*Type.*—Single.
*Blooming habit.*—Spring to autumn.
*Quantity of inflorescences per plant.*—10 to 12.
*Lastingness of the inflorescences on the plant.*—9 to 12 days.
*Fragrance.*—Absent.
*Inflorescence diameter.*—4.5 cm to 5.5 cm.
*Disc diameter.*—1.2 cm to 1.4 cm.

Disc florets:
*Quantity per inflorescence.*—90 to 100.
*Shape.*—Oblanceolate.
*Tube color* (*both closed and mature*).—RHS 1D.
*Length.*—0.5 cm.
*Diameter* (*at apex*).—0.1 cm.
*Apex.*—Obtuse.
*Apex color.*—RHS 1D.
*Base.*—Fused to form a tube.
*Margin.*—Entire.

Ray florets:
*Quantity per inflorescence.*—22.
*Shape.*—Oblanceolate.
*Color.*—Upper surface: RHS 13C at the top and RHS 70C. Lower surface: RHS 13C with longitudinal stripes of RHS 199C.
*Length.*—3.5 cm to 4.2 cm.
*Width.*—0.8 cm to 1.1 cm.
*Apex.*—Obtuse.
*Base.*—Acute.
*Margin.*—Entire.
*Texture.*—Smooth.

Peduncle:
*Length.*—Up to 14.0 cm.
*Diameter.*—0.2 cm.
*Texture.*—Rough.
*Color.*—RHS 137D.

Phyllaries:
*Arrangement.*—Single.
*Observed quantity per inflorescence.*—Approximately 22.
*Shape.*—Lanceolate.
*Color.*—Upper surface: RHS 137B. Lower surface: RHS 137D.
*Length.*—1.1 cm.
*Width.*—0.15 cm.
*Apex.*—Acute.
*Base.*—Obtuse.
*Margin.*—Entire.
*Texture.*—Rough.

Reproductive organs:
*Androecium.*—Location: Base of the disc floret corolla. Stamens: Quantity: 90 to 100. Shape: Filamentous. Color: RHS 155A. Filament length: 0.7 cm. Filament diameter: 0.08 cm. Anther: Shape: Elliptical. Color: RHS 202A. Length: 0.35 cm. Diameter: 0.05 cm. Pollen: Color: RHS 14A. Amount: Abundant.
*Gynoecium.*—Location: Base of the ray florets; stigmas in disc florets are degenerated and non-functional. Pistils: Number: 22. Length: 0.5 cm. Diameter: 0.02 cm. Stigma: Color: RHS N77A. Shape: Bipartite. Length: 0.18 cm. Diameter: 0.02 cm. Style: Color: RHS 3D. Length: 0.32 cm. Diameter: 0.02 cm. Shape: Filamentous.

Fruit and seed set: Seed set was observed.

Disease and insect/pest resistance: No specific observations were made.

COMPARISON WITH PARENTAL AND COMMERCIAL VARIETY

'KLEOE11189' differs from the female parental *osteospermum* plant 'KLEOE09175' (U.S. Plant Pat. No. 22,054) in that 'KLEOE11189' has a spreading growth habit and good branching, whereas 'KLEOE09175' has an erect growth habit and medium branching.

'KLEOE11189' differs from the male parental *osteospermum* plant 'OE 06 0119' in that 'KLEOE11189' has a spreading growth habit and good branching, whereas 'OE 06 0119' has medium branching.

We claim:

1. A new and distinct variety of *osteospermum* plant named 'KLEOE11189' as shown and described herein.

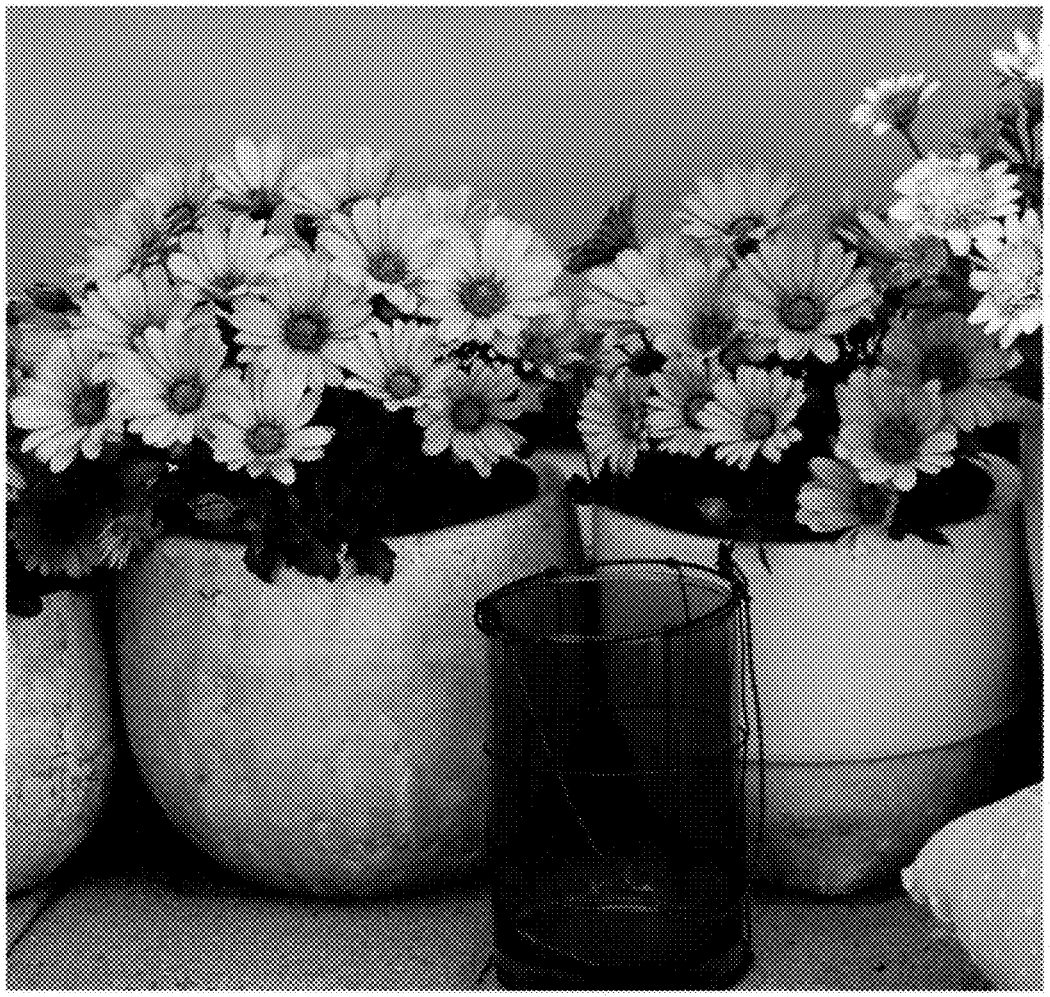

* * * * *